United States Patent [19]
Warman et al.

[11] Patent Number: 5,840,079
[45] Date of Patent: Nov. 24, 1998

[54] METHOD AND APPARATUS FOR TREATMENT OF ATRIAL FIBRILLATION

[75] Inventors: Eduardo N. Warman, Maple Grove; Luc R. Mongeon, Minneapolis, both of Minn.

[73] Assignee: Medtronic, Inc., Minneapolis, Minn.

[21] Appl. No.: 827,401

[22] Filed: Mar. 27, 1997

[51] Int. Cl.$^6$ .................................................. A61N 1/39
[52] U.S. Cl. ............................................................. 607/4
[58] Field of Search ................................. 607/4, 5, 9, 14

[56] References Cited

U.S. PATENT DOCUMENTS

| | | |
|---|---|---|
| 5,220,917 | 6/1993 | Cammilli et al. . |
| 5,265,600 | 11/1993 | Adams et al. ............................. 607/4 |
| 5,282,837 | 2/1994 | Adams et al. . |
| 5,356,425 | 10/1994 | Bardy et al. . |
| 5,480,413 | 1/1996 | Greenhut et al. . |
| 5,527,344 | 6/1996 | Arzbaecher et al. . |
| 5,549,642 | 8/1996 | Min et al. . |
| 5,562,708 | 10/1996 | Combs et al. . |

*Primary Examiner*—Scott M. Getzow
*Attorney, Agent, or Firm*—Reed A. Duthler; Harold R. Patton

[57] ABSTRACT

A method of and apparatus for delivering ventricular pacing pulses to terminate high rate atrial tachyarrhythmias including fibrillation or flutter or to reduce the requirements for termination of atrial fibrillation or flutter. In response to detected atrial fibrillation or flutter, the apparatus delivers ventricular pacing pulses at a lower rate, for example one third or half of the preceding base pacing rate, for a defined, limited period of time. After delivery of the low rate ventricular pacing pulses for the defined time period, if the high rate atrial tachyarrhythmia is not terminated, an additional therapy such a high energy defibrillation pulse or pacing level pulse trains may be applied to the atria. Prior to the delivery of low rate ventricular pacing pulses, the apparatus may deliver a higher rate of ventricular pacing pulses, for example twice the preceding base pacing rate, so that the transition in rates occurring on delivery of the low rate pulses is made more pronounced.

18 Claims, 6 Drawing Sheets

METHOD AND APPARATUS FOR TREATMENT OF ATRIAL FIBRILLATION

BACKGROUND OF THE INVENTION

The present invention relates to medical stimulators generally, and more particularly to implantable pacemakers and pacemaker/cardioverter/defibrillators.

Implantable devices intended for treatment of atrial fibrillation generally fall into five groups, including atrial defibrillators, atrial burst stimulators, parasympathetic nerve stimulators, ventricular rate stabilization pacemakers and drug dispensers. Atrial defibrillators as disclosed in U.S. Pat. No. 5,282,837, issued to Adams et al and U.S. Pat. No. 5,549,642, issued to Min et al. deliver high energy shocks to the atrium to terminate atrial fibrillation. While effective, such shocks may be painful to the patient at the energy level required for defibrillation. Atrial burst stimulators as disclosed in U.S. Pat. No. 5,562,708, issued to Combs et al. and in pending, allowed U.S. Pat. application Ser. No. 08/627, 959, by Mongeon et al, filed Apr. 2, 1996 deliver pacing level pulse trains to one or more sites on the atria to stimulate atrial muscle tissue in an attempt to terminate atrial fibrillation. This therapy, while painless, is believed likely to be effective in a smaller percentage of cases than defibrillation. Such pulse trains may also be delivered in conjunction with delivery of a defibrillation pulse as in U.S. Pat. application Ser. No. 08/495,251, filed Jun. 27, 1995 by Min et al. Parasympathetic nerve stimulators as disclosed in. U.S. Pat. No. 5,356,425 issued to Bardy deliver pulse trains to stimulate the ganglia associated with the AV node to regulate ventricular rate during atrial fibrillation, but do not attempt to terminate atrial fibrillation. Ventricular rate stabilization pacemakers as disclosed in U.S. Pat. No. 5,480,413 issued to Greenhut et al. deliver pacing pulses to the ventricle in an attempt to regularize the ventricular rhythm during atrial fibrillation, but do not attempt by this mechanism to terminate atrial fibrillation. Implantable drug dispensers as disclosed in U.S. Pat. No. 5,220,917, issued to Cammilli and U.S. Pat. No. 5,527,344, issued to Arzbaecher deliver drugs to the heart in an attempt to chemically defibrillate. None of the above described devices are yet commercially available.

Presently, one often used approach to treating atrial fibrillation is to ablate the AV node, so that the rapid, irregular electrical signals associated with atrial fibrillation the atrium do not trigger ventricular depolarizations. This treatment eliminates some symptoms of atrial fibrillation, but does not terminate the fibrillation. Patients in whom this procedure is performed usually also require the implantation of a ventricular pacemaker, as their underlying ventricular rate is typically not adequate to support normal activities.

SUMMARY OF THE INVENTION

The present invention is directed toward a method of and apparatus for delivering ventricular pacing pulses to terminate high rate atrial tachyarrhythmias including fibrillation or flutter or to reduce the requirements for termination of atrial fibrillation or flutter. The invention is believed particularly desirable for use in patients who have previously undergone ablation of the AV node as discussed above. In response to detected atrial fibrillation or flutter, the apparatus delivers ventricular pacing pulses at a lower rate, for example one third or half of the preceding base pacing rate, for a defined, limited period of time. The inventors have through testing determined that such low rate pacing can be effective to reduce the average cycle length of concurrent atrial fibrillation and can in some cases cause termination of atrial fibrillation. It is believed that the beneficial effects of low rate ventricular pacing will also result in some patients, in the case of atrial flutter.

After the delivery of the low rate ventricular pacing pulses for the defined time period, if the high rate atrial tachyarrhythmia is not terminated, an additional therapy such a high energy defibrillation pulse or pacing level pulse trains may be applied to the atria, based on the understanding that even if the prior delivered ventricular pacing pulses were ineffective to terminate the arrhythmia, they may still reduce the requirements for termination of the arrhythmia. For example, pacing level anti-atrial fibrillation therapies may be effective a larger percentage of the time and/or the atrial defibrillation threshold may be reduced, either of which results provides an increased opportunity for pain-free termination of atrial fibrillation. Low rate ventricular pacing may be continued during the delivery of the additional therapy.

In some embodiments of the invention, prior to the delivery of low rate ventricular pacing pulses, the apparatus may deliver a higher rate of ventricular pacing pulses, for example twice the preceding base pacing rate, so that the transition in rates occurring on delivery of the low rate pulses is made more pronounced. In some embodiments the invention may provide ventricular pacing as the only therapy. In other embodiments electrical stimulation of the atria may also be included. In the context of a device operating in VVI or VOO mode, the base pacing rate and the rates of the high and low rate ventricular pacing therapies may be programmed by the Physician. In the context of a pacemaker employing a physiologic sensor to regulate the base pacing rate as a function of cardiac demand, the rates of low and high rate ventricular pacing therapies provided may be programmed by the physician or automatically adjusted by the pacemaker to be below and above the sensor defined base pacing rate, respectively.

DETAILED DESCRIPTION OF THE PREFERRED EMBODIMENT

Figure 1:
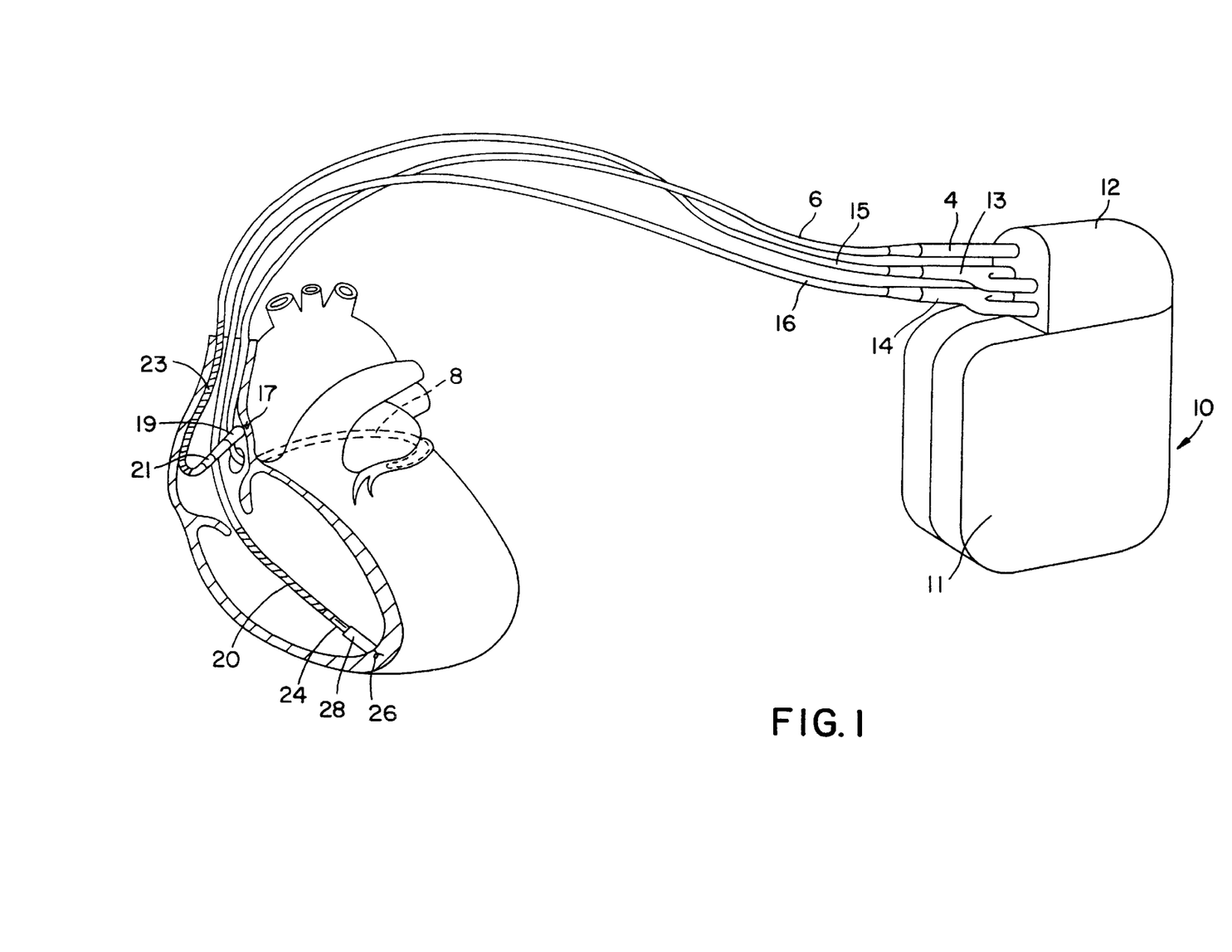
FIG. 1 illustrates a first embodiment of an implantable pacemaker/cardioverter/defibrillator according to the present invention.

FIG. 1 illustrates a defibrillator and lead set according to the present invention. The ventricular includes an elongated insulative lead body 16, carrying three concentric coiled conductors, separated from one another by tubular insulative sheaths. Located adjacent the distal end of the lead are a ring electrode 24, an extendable helix electrode 26, mounted retractably within an insulative electrode head 28, and an elongated coil electrode 20. Each of the electrodes is coupled to one of the coiled conductors within the lead body 16. Electrodes 24 and 26 are employed for cardiac pacing and for sensing ventricular depolarizations. At the proximal end of the lead is a bifurcated connector 14 which carries three electrical connectors, each coupled to one of the coiled conductors. The defibrillation electrode 20 may be fabricated from platinum, platinum alloy or other materials known to be usable in implantable defibrillation electrodes and may be about 5 cm in length.

The atrial/SVC lead includes an elongated insulative lead body 15, carrying three concentric coiled conductors, separated from one another by tubular insulative sheaths, corresponding to the structure of the ventricular lead. Located adjacent the J-shaped distal end of the lead are a ring electrode 21 and an extendable helix electrode 17, mounted retractably within an insulative electrode head 19. Each of the electrodes is coupled to one of the coiled conductors within the lead body 15. Electrodes 17 and 21 are employed for atrial pacing and for sensing atrial depolarizations. An elongated coil electrode 23 is provided, proximal to electrode 21 and coupled to the third conductor within the lead body 15. Electrode 23 preferably is 10 cm in length or greater and is configured to extend from the SVC toward the tricuspid valve. In one preferred embodiment tested by the inventors, approximately 5 cm of the right atrium/SVC electrode was located in the right atrium, with the remaining 5 cm located in the SVC. At the proximal end of the lead is a bifurcated connector 13 which carries three electrical connectors, each coupled to one of the coiled conductors.

The coronary sinus lead includes an elongated insulative lead body 6, carrying one coiled conductor, coupled to an elongated coiled defibrillation electrode 8. Electrode 8, illustrated in broken outline, is located within the coronary sinus and great vein of the heart. At the proximal end of the lead is a connector plug 4 which carries an electrical connector, coupled to the coiled conductor. The coronary sinus/great vein electrode 8 may be about 5 cm in length.

An implantable pacemaker/cardioverter/defibrillator 10 is shown in combination with the leads, with the lead connector assemblies 4, 13 and 14 inserted into the connector block 12. Optionally, insulation of the outward facing portion of the housing 11 of the pacemaker/cardioverter/defibrillator 10 may be provided using a plastic coating, for example parylene or silicone rubber, as is currently employed in some unipolar cardiac pacemakers. However, the outward facing portion may instead be left uninsulated, or some other division between insulated and uninsulated portions may be employed. The uninsulated portion of the housing 11 optionally serves as a subcutaneous defibrillation electrode, used to defibrillate either the atria or ventricles.

Figure 2:
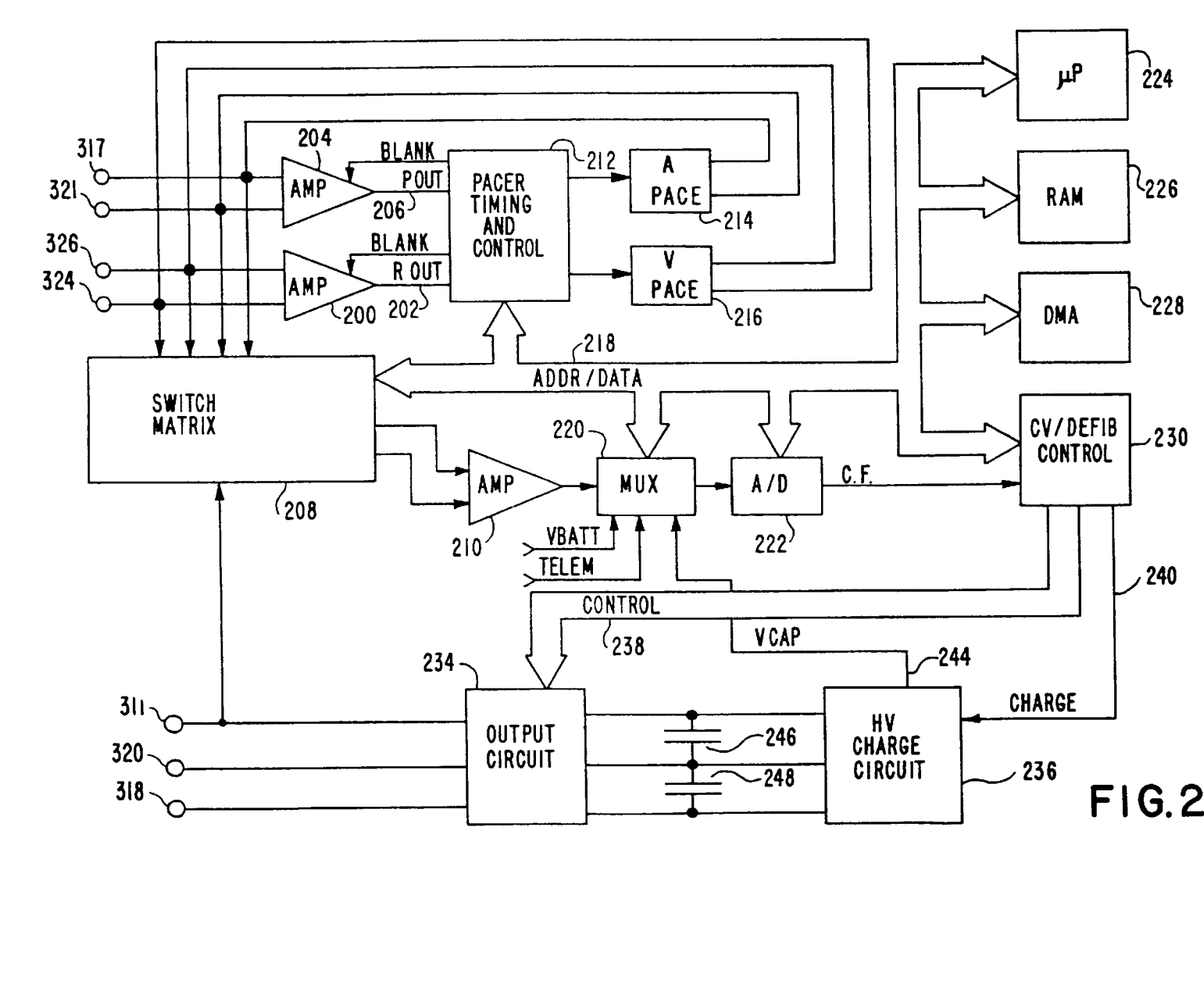
FIG. 2 illustrates a functional schematic diagram of an implantable pacemaker/cardioverter/defibrillator embodying the invention.

FIG. 2 is a functional schematic diagram of an implantable pacemaker/cardioverter/defibrillator in which the present invention may usefully be practiced. This diagram should be taken as exemplary of the type of device in which the invention may be embodied, and not as limiting, as it is believed that the invention may usefully be practiced in a wide variety of device implementations, including pacemakers without the capability of delivering electrical therapies to the atria and pacemaker/defibrillators which do not provide pacing pulse level anti-atrial fibrillation therapies.

The device is provided with an electrode system including electrodes as illustrated in FIG. 1, but may also be provided with alternate electrode systems of the type conventionally used for pacing and defibrillation. The correspondence to the electrodes illustrated in FIG. 1 is as follows. Optional electrode 310 corresponds to electrode 11, and is the uninsulated portion of the housing of the implantable pacemaker/cardioverter/defibrillator. Electrode 320 corresponds to electrode 20 and is a defibrillation electrode located in the right ventricle. Electrode 311 corresponds to electrode 23, and is located in the right atrium and SVC. Electrode 318 corresponds to electrode 8 and is a defibrillation electrode located in the coronary sinus and great vein. Electrodes 324 and 326 correspond to electrodes 24 and 26, and are used for sensing and pacing in the ventricle. Electrodes 317 and 321 correspond to electrodes 17 and 19 and are used for pacing and sensing in the atrium.

Electrodes 310, 311, 318 and 320 are coupled to high voltage output circuit 234. High voltage output circuit 234 includes high voltage switches controlled by CV/defib control logic 230 via control bus 238. The switches within circuit 234 control which electrodes are employed and which are coupled to the positive and negative terminals of the capacitor bank including capacitors 246 and 248 during delivery of the defibrillation pulses.

Electrodes 424 and 326 are located on or in the ventricle and are coupled to the R-wave amplifier 200, which preferably takes the form of an automatic gain controlled amplifier providing an adjustable sensing threshold as a function of the measured R-wave amplitude. A signal is generated on R-out line 202 whenever the signal sensed between electrodes 612 and 614 exceeds the present sensing threshold.

Electrodes 317 and 321 are located on or in the atrium and are coupled to the P-wave amplifier 204, which preferably also takes the form of an automatic gain controlled amplifier providing an adjustable sensing threshold as a function of the measured P-wave amplitude. A signal is generated on P-out line 206 whenever the signal sensed between electrodes 617 and 621 exceeds the present sensing threshold. The general operation of the R-wave and P-wave amplifiers 200 and 204 may correspond to that disclosed in U.S. Pat. No. 5,117,824, by Keimel, et al., issued Jun. 2, 1992, for an Apparatus for Monitoring Electrical Physiologic Signals, incorporated herein by reference in its entirety.

Switch matrix 208 is used to select which of the available electrodes are coupled to wide band (0.5–200 Hz) amplifier 210 for use in digital signal analysis. Selection of electrodes is controlled by the microprocessor 224 via data/address bus 218, which selections may be varied as desired. Signals from the electrodes selected for coupling to bandpass amplifier 210 are provided to multiplexer 220, and thereafter converted to multi-bit digital signals by A/D converter 222, for storage in random access memory 226 under control of direct memory access circuit 228. Microprocessor 224 may employ digital signal analysis techniques to characterize the digitized signals stored in random access memory 226 to recognize and classify the patient's heart rhythm employing any of the numerous signal processing methodologies known to the art.

The remainder of the circuitry is dedicated to the provision of cardiac pacing, cardioversion and defibrillation therapies, and, for purposes of the present invention may correspond to circuitry known in the prior art. An exemplary apparatus is disclosed of accomplishing pacing, cardioversion and defibrillation functions follows. The pacer timing/control circuitry 212 includes programmable digital counters which control the basic time intervals associated with DDD, VVI, DVI, VDD, AAI, DDI and other modes of single and dual chamber pacing well known to the art. Circuitry 212 also controls escape intervals associated with anti-tachyarrhythmia pacing in both the atrium and the ventricle, employing any anti-tachyarrhythmia pacing therapies known to the art.

Intervals defined by pacing circuitry 212 include atrial and ventricular pacing escape intervals, the refractory periods during which sensed P-waves and R-waves are ineffective to restart timing of the escape intervals and the pulse widths of the pacing pulses. The durations of these intervals are determined by microprocessor 226, in response to stored data in memory 226 and are communicated to the pacing circuitry 212 via address/data bus 218. Pacer circuitry 212 also determines the amplitude of the cardiac pacing pulses under control of microprocessor 224.

During pacing, the escape interval counters within pacer timing/control circuitry 212 are reset upon sensing of R-waves and P-waves as indicated by a signals on lines 202 and 206, and in accordance with the selected mode of pacing on timeout trigger generation of pacing pulses by pacer output circuitry 214 and 216, which are coupled to electrodes 317, 321, 324 and 326. The escape interval counters are also reset on generation of pacing pulses, and thereby control the basic timing of cardiac pacing functions, including anti-tachyarrhythmia pacing. The durations of the intervals defined by the escape interval timers are determined by microprocessor 224, via data/address bus 218. The value of the count present in the escape interval counters when reset by sensed R-waves and P-waves may be used to measure the durations of R-R intervals, P-P intervals, P-R intervals and R-P intervals, which measurements are stored in memory 226 and used to detect the presence of tachyarrhythmias.

Microprocessor 224 operates under control of a stored program located in read only memory therein and operates as an interrupt driven device, responsive to interrupts from pacer timing/control circuitry 212 corresponding to the occurrence of sensed P-waves and R-waves and corresponding to the generation of cardiac pacing pulses. These interrupts are provided via data/address bus 218. Any necessary mathematical calculations to be performed by microprocessor 224 and any updating of the values or intervals controlled by pacer timing/control circuitry 212 take place following such interrupts.

For example, in response to a sensed or paced ventricular depolarization or R-wave, the intervals separating that R-wave from the immediately preceding R-wave, paced or sensed (R-R interval) and the interval separating the paced or sensed R-wave from the preceding atrial depolarization, paced or sensed (P-R interval) may be stored. Similarly, in response to the occurrence of a sensed or paced atrial depolarization (P-wave), the intervals separating the sensed P-wave from the immediately preceding paced of sensed atrial contraction (P-P Interval) and the interval separating the sensed P-wave from the immediately preceding sensed or paced ventricular depolarization (R-P interval) may be stored. Preferably, a portion of the memory 226 (FIG. 4) is configured as a plurality of recirculating buffers, capable of holding a preceding series of measured intervals, which may be analyzed in response to the occurrence of a pace or sense interrupt to determine whether the patient's heart is presently exhibiting atrial or ventricular tachyarrhythmia.

Detection of atrial or ventricular tachyarrhythmias, as employed in the present invention, may correspond to tachyarrhythmia detection algorithms known to the art. For example, presence of atrial or ventricular tachyarrhythmia may be confirmed by means of detection of a sustained series of short R-R or P-P intervals of an average rate indicative of tachyarrhythmia or an unbroken series of short R-R or P-P intervals. The suddenness of onset of the detected high rates, the stability of the high rates, or a number of other factors known to the art may also be measured at this time. Appropriate ventricular tachyarrhythmia detection methodologies measuring such factors are described in U.S. Pat. No. 4,726,380, issued to Vollmann, U.S. Pat. No. 4,880,005, issued to Pless et al. and U.S. Pat. No. 4,830,006, issued to Haluska et al., all incorporated herein by reference in their entireties. An additional set of tachycardia recognition methodologies is disclosed in the article "Onset and Stability for Ventricular Tachyarrhythmia Detection in an Implantable Pacer-Cardioverter-Defibrillator" by Olson et al., published in Computers in Cardiology, Oct. 7–10, 1986, IEEE Computer Society Press, pages 167–170, also incorporated herein in its entirety. However, one of the advantages of the present invention is that it is believed practicable in conjunction with most prior art tachycardia detection algorithms. Atrial fibrillation detection methodologies in particular are disclosed in Published PCT application Ser. No. US92/02829, Publication No. W092/18198, by Adams et al., and in the article "Automatic Tachycardia Recognition", by Arzbaecher et al., published in PACE, May–June, 1984, pp. 541–547, both of which are incorporated by reference in their entireties.

In a preferred embodiment of the invention, the atrial fibrillation detection methodologies may be those set forth in U.S. Pat. application Ser. No. 08/649,145 by Gillberg et al., filed on May 14, 1996 and incorporated herein by reference in its entirety. In the event that an atrial or ventricular tachyarrhythmia is detected, and a pacing level anti-arrhythmia pulse regimen is desired, appropriate timing intervals for controlling generation of pacing level therapies are loaded from microprocessor 224 into the pacer timing and control circuitry 212, to control the operation of the escape interval counters therein and to define refractory periods during which detection of R-waves and P-waves is ineffective to restart the escape interval counters.

Alternatively, circuitry for controlling the timing and generation of anti-tachycardia pacing pulses as described in U.S. Pat. No. 4,577,633, issued to Berkovits et al. on Mar. 25, 1986, U.S. Pat. No. 4,880,005, issued to Pless et al. on Nov. 14, 1989, U.S. Pat. No. 4,726,380, issued to Vollmann et al. on Feb. 23, 1988 and U.S. Pat. No. 4,587,970, issued to Holley et al. on May 13, 1986, all of which are incorporated herein by reference in their entireties may also be used.

In the event that generation of a cardioversion or defibrillation pulse is required, microprocessor 224 employs the an escape interval counter to control timing of such cardioversion and defibrillation pulses, as well as associated refractory periods. In response to the detection of atrial or ventricular fibrillation or tachyarrhythmia requiring a cardioversion pulse, microprocessor 224 activates cardioversion/defibrillation control circuitry 230, which initiates charging of the high voltage capacitors 246 and 248 via charging circuit 236, under control of high voltage charging control lines 240 and 242. The voltage on the high voltage capacitors is monitored via VCAP line 244, which is passed through multiplexer 220 and in response to reaching a predetermined value set by microprocessor 224, results in generation of a logic signal on Cap Full (CF) line 254, terminating charging. Thereafter, timing of the delivery of the defibrillation or cardioversion pulse is controlled by pacer timing/control circuitry 212. Following delivery of the fibrillation or tachycardia therapy the microprocessor then returns the device to cardiac pacing and awaits the next successive interrupt due to pacing or the occurrence of a sensed atrial or ventricular depolarization.

Systems for delivery and synchronization of ventricular cardioversion and defibrillation pulses and for controlling the timing functions related to them are disclosed in more detail in commonly assigned U.S. Pat. No. 5,188,105 issued to Keimel, and U.S. Pat. No. 5,193,536 issued to Mehra, both incorporated herein by reference in their entireties. The synchronization methodology for ventricular cardioversion pulses disclosed in the Mehra patent may likewise be employed to synchronize delivery of atrial cardioversion and defibrillation pulses, by synchronizing the delivered pulse to one or the last of a series of ventricular pacing pulses. An alternative method of synchronization of atrial defibrillation and cardioversion pulses is disclosed in U.S. Pat. No. 5,411,524 issued to Mehra, also incorporated herein by reference in its entirety.

In the illustrated device, delivery of the cardioversion or defibrillation pulses is accomplished by output circuit 234, under control of control circuitry 230 via control bus 238. Output circuit 234 determines whether a monophasic or biphasic pulse is delivered, the polarity of the electrodes and which electrodes are involved in delivery of the pulse. Output circuit 234 also includes high voltage switches which control whether electrodes are coupled together during delivery of the pulse. Alternatively, electrodes intended to be coupled together during the pulse may simply be permanently coupled to one another, either exterior to or interior of the device housing, and polarity may similarly be pre-set, as in current implantable defibrillators. An example of output circuitry for delivery of biphasic pulse regimens to multiple electrode systems may be found in the above cited patent issued to Mehra and in U.S. Pat. No. 4,727,877, incorporated by reference in its entirety.

An example of circuitry which may be used to control delivery of monophasic pulses is set forth in commonly assigned U.S. Pat. No. 5,163,427, by Keimel, issued Nov. 17, 1992, also incorporated herein by reference in its entirety. However, output control circuitry as disclosed in U.S. Pat. No. 4,953,551, issued to Mehra et al. on Sep. 4, 1990 or U.S. Pat. No. 4,800,883, issued to Winstrom on Jan. 31, 1989 both incorporated herein by reference in their entireties, may also be used in conjunction with a device embodying the present invention for delivery of biphasic pulses.

In the event that, as in FIG. 1, both atrial and ventricular defibrillation are available, ventricular defibrillation may be accomplished using higher pulse energy levels than required for atrial defibrillation and may employ the same or a different electrode set. For example, electrodes 310, 311, 318 and 320 or only electrodes 311, 318 and 320 may be employed for atrial defibrillation. Electrodes 311, 320 and 310 might be employed for ventricular defibrillation, with electrode 311 (right atrium/SVC) coupled to electrode 310 (device housing). Alternatively, electrodes 310, 318 and 320 may be employed, with electrode 318 (coronary sinus/great vein) coupled to electrode 310. As a further alternative, electrodes 311, 310, 318 and 323 might all be employed for ventricular defibrillation, with electrodes 310, 311 and 323 coupled in common. As yet another alternative, only electrodes 310 and 320 might be employed for ventricular defibrillation. added or substituted for either of electrodes 311 or 318 for treating ventricular fibrillation.

One particularly desirable embodiment of the invention employs only the right atrial/SVC electrode 311, the coronary sinus/great vein electrode 318 and the right ventricular electrode 320. During atrial defibrillation, electrodes 320 and 318 are coupled in common with one another, and the atrial defibrillation pulse is delivered between these electrodes and electrode 311. During ventricular defibrillation, electrodes 311 and 318 are coupled in common with one another, and the ventricular defibrillation pulse is delivered between these electrodes and electrode 320. This particular set of electrodes thus provides optimized defibrillation pulse regimens for both atrial and ventricular defibrillation, by simply switching the connection of the coronary sinus/great vein electrode.

In modern implantable cardioverter/defibrillators, the particular therapies are programmed into the device ahead of time by the physician, and a menu of therapies is typically provided. For example, on initial detection of an atrial or ventricular tachycardia, an anti-tachycardia pacing therapy may be selected and delivered to the chamber in which the tachycardia is diagnosed or to both chambers. On redetection of tachycardia, a more aggressive anti-tachycardia pacing therapy may be scheduled. If repeated attempts at anti-tachycardia pacing therapies fail, a higher level cardioversion pulse may be selected thereafter. Therapies for tachycardia termination may also vary with the rate of the detected tachycardia, with the therapies increasing in aggressiveness as the rate of the detected tachycardia increases. For example, fewer attempts at anti-tachycardia pacing may be undertaken prior to delivery of cardioversion pulses if the rate of the detected tachycardia is above a preset threshold. The references cited above in conjunction with descriptions of prior art tachycardia detection and treatment therapies are applicable here as well.

In the event that atrial or ventricular fibrillation is identified, the typical therapy will be delivery of a high amplitude defibrillation pulse, typically in excess of 10 joules in the case of ventricular fibrillation and about 1 joule or less in the case of atrial defibrillation. Lower energy levels will be employed for cardioversion. As in the case of currently available implantable pacemakers/cardioverter/ defibrillators, and as discussed in the above-cited references, it is envisioned that the amplitude of the defibrillation pulse may be incremented in response to failure of an initial pulse or pulses to terminate fibrillation. Prior art patents illustrating such pre-set therapy menus of anti-tachyarrhythmia therapies include the above-cited U.S. Pat. No. 4,830,006, issued to Haluska, et al., U.S. Pat. No. 4,727,380, issued to Vollmann et al. and U.S. Pat. No. 4,587,970, issued to Holley et al.

Figure 3:
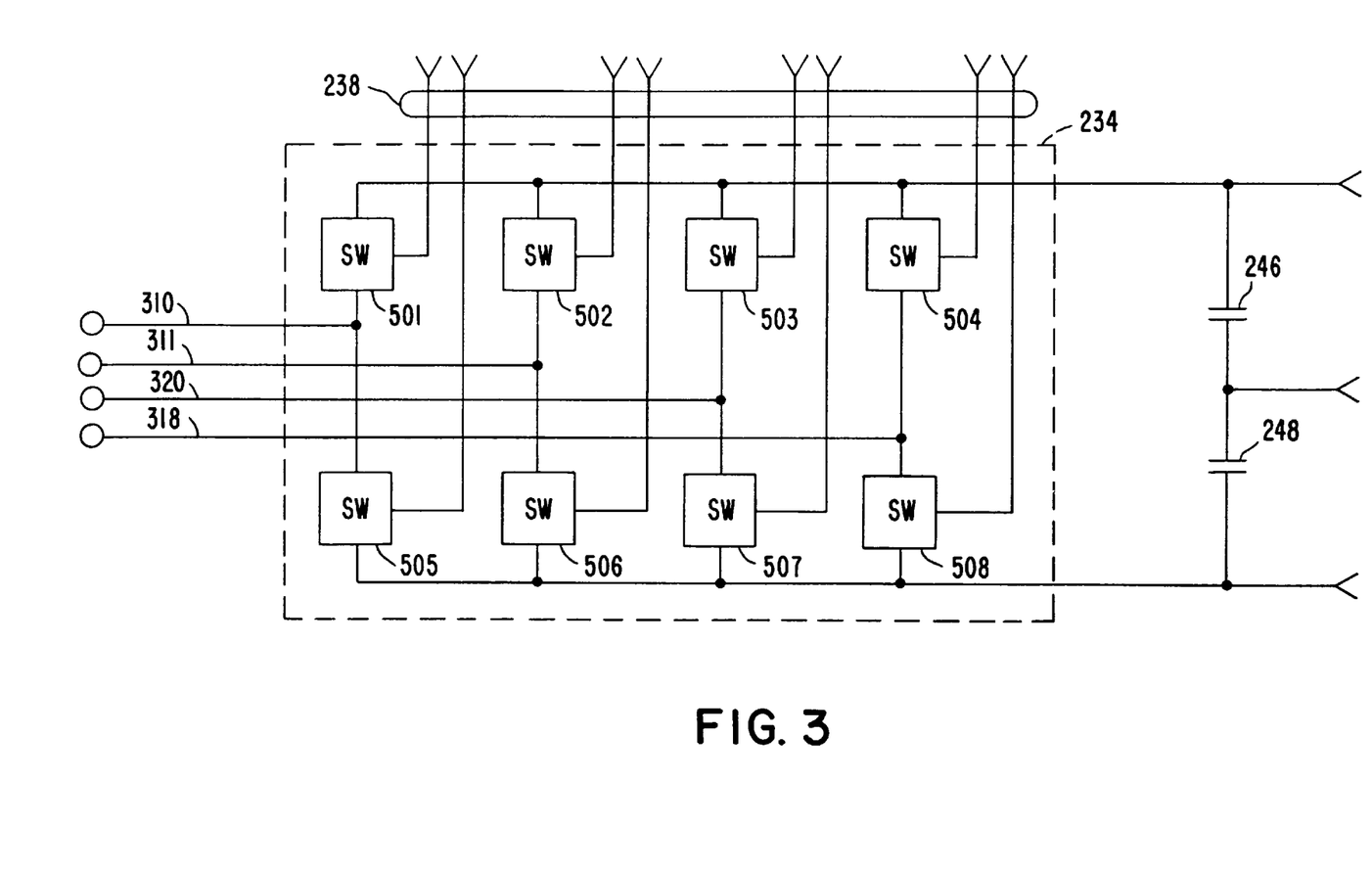
FIG. 3 illustrates a functional schematic diagram of the high voltage switching circuitry of the device illustrated in FIG. 2.

FIG. 3 is a functional schematic diagram of switching circuitry which may be employed in high voltage output circuit 234, illustrated in FIG. 2. The circuitry includes eight high voltage switches 501, 502, 503, 504, 505, 506, 507 and 508, which are individually controlled by signals on control bus 238. These switches allow connection of any of the four electrodes 301, 311, 320 and 318 to either the positive or the negative terminal of the capacitor and comprising capacitors 246 and 248. As illustrated, any combination of electrodes may be selected, any polarities desired may be provided, and monophasic or biphasic pulses may be delivered, depending upon control signals on control bus 238. In the event that a reduced set of available electrode configurations is desired, the switching circuitry may be simplified. For example, if two electrodes (e.g. 318 and 320) are hard wired together, either in the connector block or in the device housing, one set of two switches (504, 508) may be deleted. Correspondingly, if only three electrodes are desired, (e.g. electrode 310 is deleted) a set of switches (501,505) may similarly be deleted. If only atrial defibrillation is desired, using only three electrodes both of these changes could be made, resulting in an output circuit employing only four switches and which corresponds to high voltage output circuits presently used in implantable ventricular defibrillators.

Figure 4:
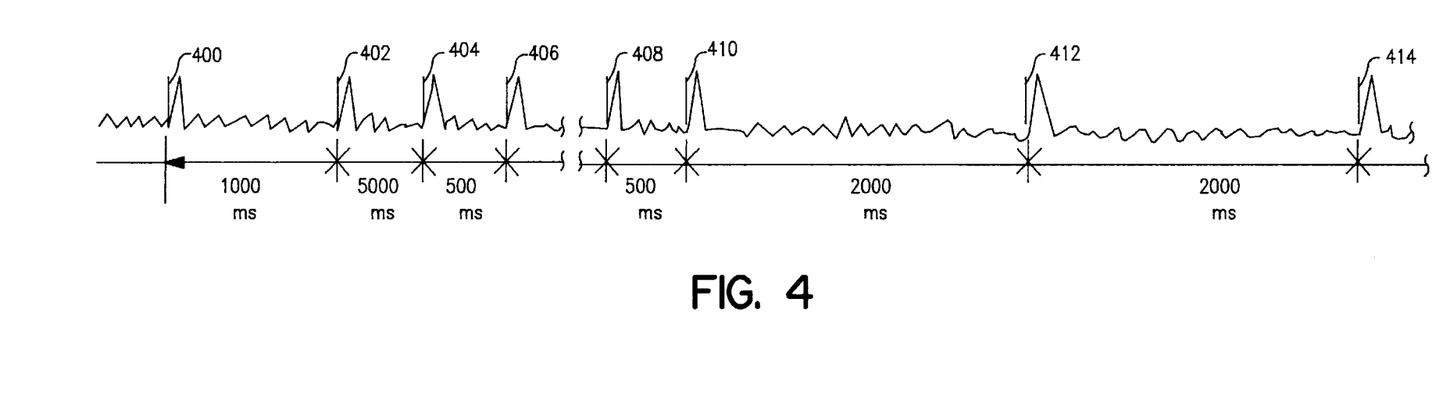
FIGS. 4 and 5 are simulated electrograms illustrating the operation of the invention.
Figure 5:
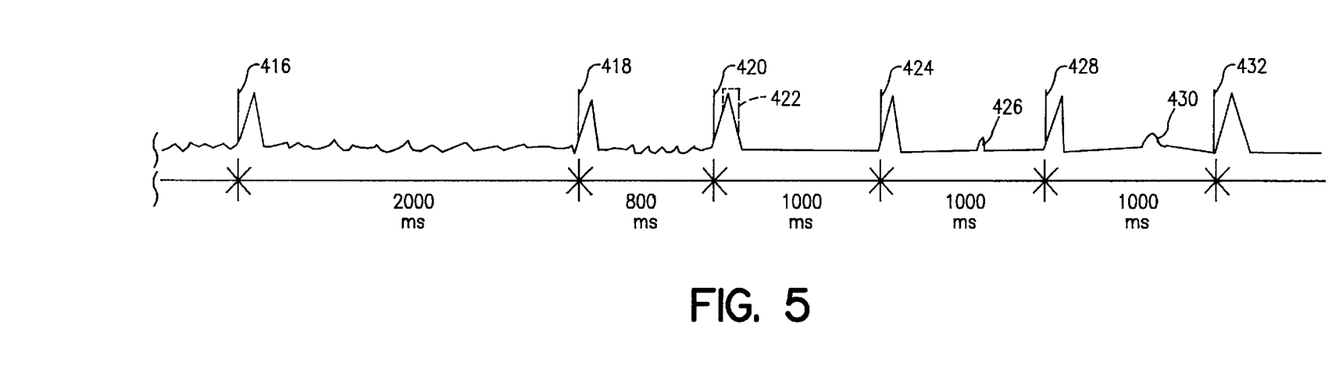

FIGS. 4 and 5 together illustrate the delivery of ventricular pacing pulses according to one embodiment of the present invention. Pacing pulses 400 and 402 are separated by 1,000 milliseconds, which should be understood to be either the programmed escape interval for normal operation during VVI or VOO pacing or the sensor indicated pacing rate for normal operation during VVIR or VOOR pacing. The irregular waveform of the baseline between pacing pulses 400 and 402 is intended to indicate the presence of atrial fibrillation, and it is to be understood that the device detects the occurrence of atrial fibrillation following delivery of pacing pulse 402. In response, the ventricular escape interval is substantially reduced, for example, one-half of the previous escape interval, and pacing pulses 404, 406, 408, 410 are delivered over a preset period of time, for example, 120 seconds. The 500 ms duration of the escape intervals during the high rate pacing therapy as illustrated may be either pre-programmed by the physician or calculated by the pacemaker based on the preceding duration of the escape interval at the base pacing rate. At 410, on expiration of the first preset time, the pacing rate is dropped to substantially below the preceding base pacing rate, for example to one-half of the preceding base pacing rate pacing rate, extending the escape interval 2,000 mi milliseconds. Pacing pulses 412, 414, 416 and 418 are delivered at this extended pulse interval, for a second period of time, for example, 120 seconds. The 2000 ms duration of the escape intervals during the low rate pacing therapy as illustrated may be either pre-programmed by the physician or calculated by the pacemaker based on the preceding duration of the escape interval at the base pacing rate.

If the apparatus embodying the invention is provided with a mechanism for delivering an additional atrial antiarrhythmia therapy such as electrically stimulating the atrium, on expiration of the second period of time, the device may initiate delivery of such additional therapy. As discussed above, the additional therapy may be a pacing pulse level therapy as discussed above or delivery of a high energy cardioversion or defibrillation shock. As illustrated in FIG. 5, an atrial defibrillation shock 422, illustrated in broken outline, is delivered synchronized to pacing pulse 420, which is delivered following a shorter escape interval of 800 milliseconds following pacing pulse 418. However, other synchronization mechanisms might also be employed. As illustrated in FIG. 5, it is to be understood that the atrial fibrillation pulse 422 has been effective in terminating atrial fibrillation, and the device returns to operation in the VOO or VVI mode at the programmed escape interval of 1,000 milliseconds, separating pacing pulses 424, 428 and 432. Normal atrial depolarizations 426 and 430 are illustrated. However in an embodiment operating in VVI mode as illustrated, the delivered ventricular pacing pulses are not be synchronized to the sensed atrial depolarizations. If the additional atrial antiarrhythmia therapy persists for a period of time, such as in the case of pacing pulse level therapies as described above, the device may continue to pace the ventricles at a low rate or may return to the base pacing rate, depending on the preferences of the physician.

While FIGS. 4 and 5 illustrate the operation of a device operating in VVI, VOO, VVIR or VOOR mode, it is also possible that the low rate ventricular pacing therapy provided by the invention can be embodied in a dual chamber pacemaker, operating in VDD or DDD mode. In such a pacemaker, it should be understood that the atrial pacing pulse generator would normally be inhibited during periods of atrial fibrillation, and that atrial synchronized ventricular pacing would correspondingly also not occur during atrial fibrillation, in order to avoid the delivery of ventricular pacing pulses at an unduly high rate. Dual chamber pacemakers having these capabilities are disclosed in U.S. Pat. No. 5,144,949, issued to Olson and in U.S. Pat. No. 4,932, 406 issued to Berkovits, both of which are incorporated herewith in their entireties. In such devices, following termination of atrial fibrillation, ventricular pacing pulses would be delivered synchronized to sensed atrial depolarizations and, if the device operates in DDD mode, atrial pacing pulses may be delivered to stimulate atrial depolarizations.

While the device as illustrated in FIG. 5 operates to immediately switch between pacing at the base pacing rate to pacing at the higher rate, in some embodiments of the invention the device may instead ramp up the pacing rate more gradually. Similarly, in some embodiments of the invention, the device may ramp down the pacing rate from the higher pacing rate or the base pacing rate to the lower pacing rate rather than switching immediately to the lower pacing rate. in such embodiments it is believed that the change in rate, even if not immediate, should still be rapid, for example occurring over a few pacing cycles, so that a relatively abrupt drop in rate is still produced.

Figure 6:
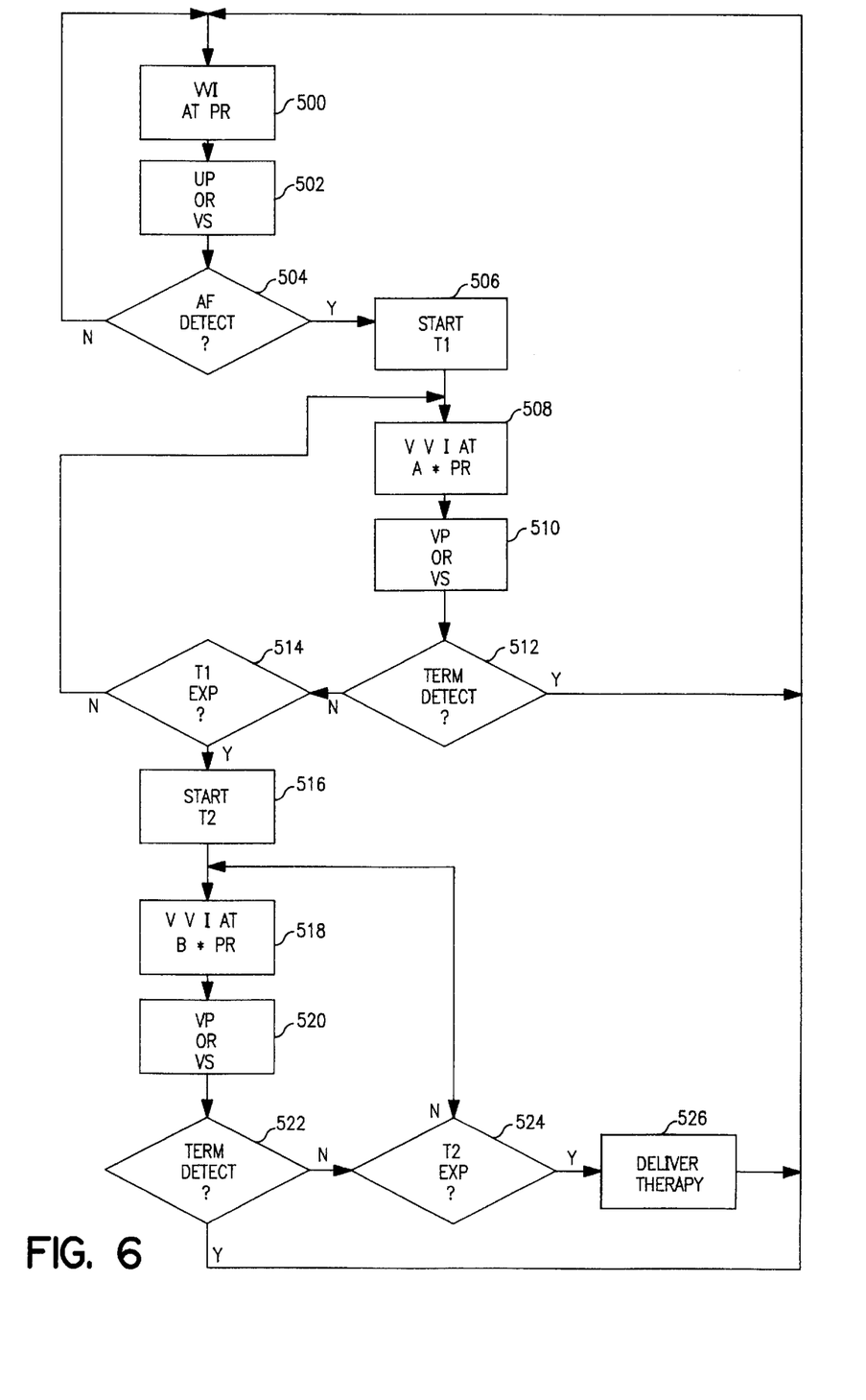
FIG. 6 is a functional flow chart illustrating the operation of a first embodiment of the invention.

FIG. 6 is a functional flow chart illustrating a first embodiment of the invention in which the device is provided with a method of delivering a therapy directed toward termination of atrial fibrillation of one of the types discussed above. It should be understood that detection of other high rate atrial tacharrhythmias such as atrial flutter may be substituted for or added to the detection and treatment of atrial fibrillation as set forth in this Figure. As in the case of the operation of the device illustrated in FIGS. 4 and 5, the device is presumed to be operating in a ventricular-only pacing mode, in this case, VVI. However, the methodology illustrated in FIG. 6 may also be adapted to a dual chamber pacemaker operable in VDD or DDD mode or to a single or dual chamber rate-responsive pacemaker, as discussed above. At 500, it is assumed that the device is operating in VVI mode, pacing at the programmed base pacing rate "PR". Following delivery of a ventricular pacing pulse or sensing of a ventricular depolarization at 502, the device checks to determine whether it has detected atrial fibrillation (or other high rate atrial tachyarrhythmia) at 504, using any of the mechanisms described above. If atrial fibrillation is not detected, the device continues to pace in VVI mode at the programmed rate.

If atrial fibrillation is detected, the device begins timing a first time interval at 506, during which the device delivers VVI pacing at a rate which is substantially greater than the pacing rate PR, for example 1.5–2.5 * PR. Following each delivered ventricular pacing pulse or sensed depolarization at 510, the device checks at 512 to determine whether atrial fibrillation has terminated, for example, by occurrence of the sequence of a predetermined number of P-P intervals in excess of a defined maximum atrial fibrillation interval duration. If termination is detected at 512, the device returns to VVI pacing at the programmed rate. If termination is not detected, the device continues pacing at A * PR until the expiration of the first time interval at 514. On expiration of the first time interval, the second time interval is initiated at 516. In an alternative embodiment of the invention, following detection of atrial fibrillation at 504, the device might proceed directly to 516, and initiate the timing of the interval during which low rate ventricular pacing pulses are generated. During the period defined by the second time interval, ventricular pacing pulses are delivered at 518 at a rate which is substantially lower than the programmed pacing rate PR, 0.3–0.5. *PR. Following delivery of a ventricular pacing pulse or a sensed depolarization at 520, the device checks at 522 to determine whether atrial fibrillation has terminated. If so, the device returns to VVI pacing at the programmed rate of 500. If not, the device continues to pace at the lower rate until expiration of the second timed interval T2 or termination of atrial fibrillation.

In the device illustrated in FIG. 6, it is assumed that a mechanism for delivering an additional anti-atrial fibrillation therapy is also included, and that on expiration of a second time interval at 524, such therapy will be delivered at 526. This therapy may be an atrial pacing pulse level therapy as described in the above cited Combs et al. and Mongeon et al. patents or may be a defibrillation or cardioversion pulse as described in the above cited Adams and Min patents.

Figure 7:
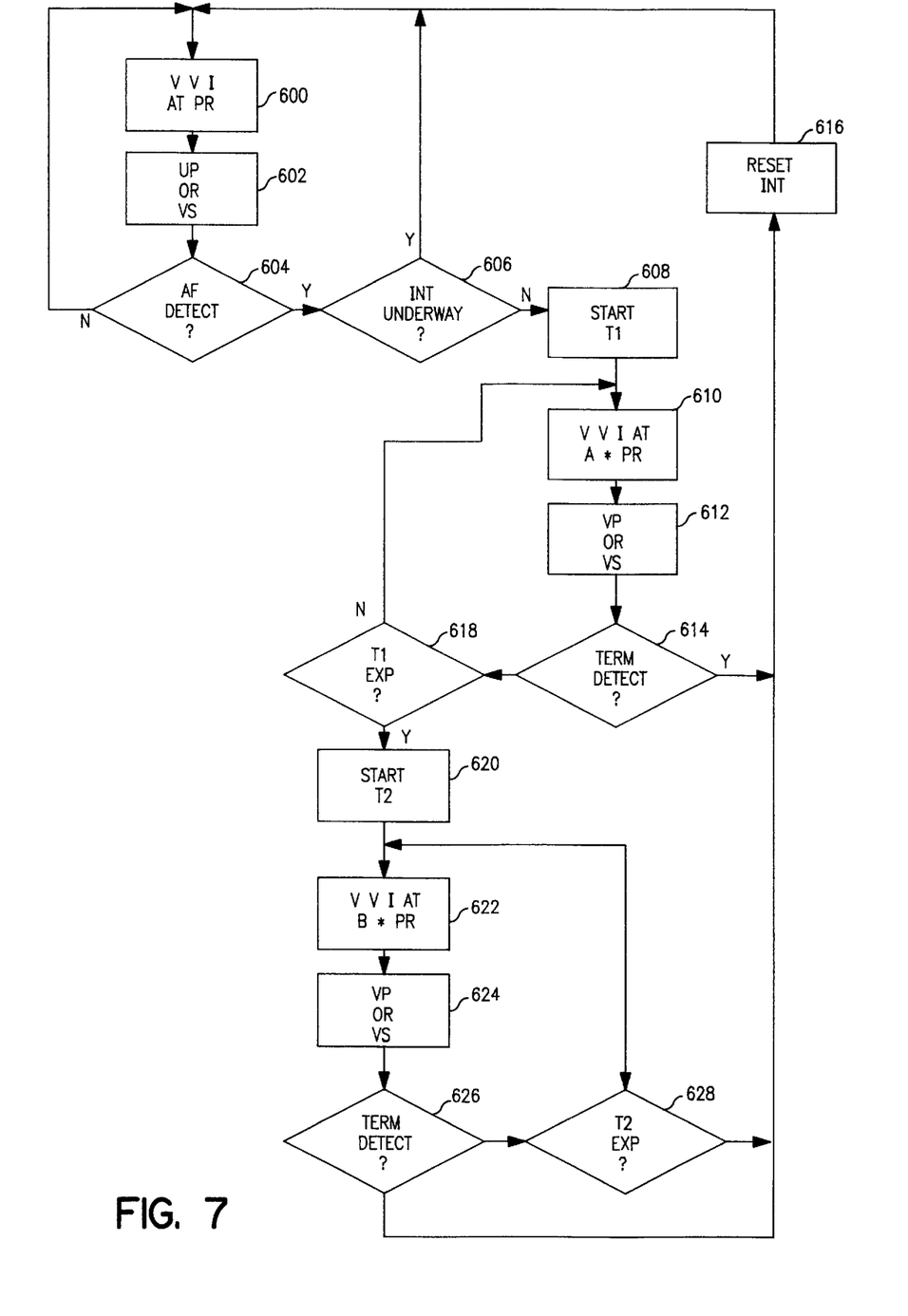
FIG. 7 is a functional flow chart illustrating the operation of a second embodiment of the invention.

FIG. 7 illustrates an alternative mode of operation for the invention as embodied in a ventricular pacemaker without the capability of delivering an additional therapy to terminate atrial fibrillation. In this embodiment, the ventricular pacing mode described above is the only therapy delivered in an attempt to terminate atrial fibrillation. As in the case of FIG. 6, it should be understood that detection of other high rate atrial tachyarrhythmias, especially atrial flutter may be added to or substituted for the detection of atrial fibrillation At 600, the device is operating in VVI mode, pacing at the programmed rate for "PR". Following a ventricular pace or ventricular sensed depolarization at 602, the device checks at 604 to determine whether atrial fibrillation (or other high rate atrial tachyarrhythmia) is present. If not, the device simply continues pacing in the VVI mode. If atrial fibrillation is present, the device checks at 606 to determine whether an inter-therapy time interval, initiated after a previous delivery of the low rate pacing therapy is still underway. If not, the device initiates the ventricular pacing therapy described above at 608 by starting timing of the first time interval. If an inter-therapy is still underway, the device simply continues pacing in the VVI mode until the inter-therapy interval expires.

During the first time interval T1, the device delivers VVI pacing at a rate substantially greater than the programmed rate, as described above. Following ventricular pacing or ventricular sensing at 612, the device checks to determine whether atrial fibrillation has terminated at 614. If so, the device resets the inter-therapy timer at 616 and returns to VVI pacing at the programmed rate. If termination is not detected, the device checks to determine whether the first time interval has expired at 618. If not, the device continues to pace at the higher pacing rate until either the first time interval expires or termination of atrial fibrillation is detected.

On expiration of interval T1, the device begins delivery of the low rate ventricular pacing pulses, by initializing the timing of the second interval at 620. In an alternative embodiment, in response to detection of atrial fibrillation at 606, the device may immediately initialize the timing of the second time interval T2 at 620 and initiate delivery of low rate ventricular pacing. During the second time interval at 622, VVI pacing is delivered at a rate substantially below the programmed rate, as described above. Following a delivered pacing pulse or sensed ventricular depolarization at 624, the device checks at 626 to determine whether atrial fibrillation has terminated. If so, it resets the inter-therapy timer and returns to VVI pacing at the programmed rate. If not, the device continues to pace at the lower pacing rate until either termination of atrial fibrillation or expiration of the second time interval. Upon expiration of the second time interval at 628, the device initiates the inter-therapy time interval and returns to VVI pacing at the programmed rate.

In this embodiment of the device, the therapy is delivered intermittently during atrial fibrillation on the assumption that it will sometimes be effective to terminate atrial fibrillation. Because atrial fibrillation is not immediately life threatening, this therapy is of benefit even if it is only occasionally capable of terminating atrial fibrillation. The therapy may be embodied by the addition only of an atrial lead for sensing atrial depolarizations and associated logic and software for detecting the occurrence of atrial fibrillation to the ventricular pacemaker the patient would be getting anyway. For a patient in whom the low rate pacing or combined high rate/low rate pacing therapy is effective to terminate atrial fibrillation, a substantial benefit is thus provided at a minimum of additional expense, and with no substantial increase in complexity of the surgery associated with the implantation of the ventricular pacemaker.

While the invention is disclosed above embodied in a dual chamber pacemaker/cardioverter/defibrillator, the invention may also be usefully practiced in substantially simpler devices. For example, the illustrated pacing and defibrillation electrodes may simply be coupled to an implantable atrial defibrillator disclosed in published PCT application Ser. No. US92/02829, Publication No. W092/18198, by Adams et al, incorporated herein by reference in its entirety. A simple device of this type is believed workable in some patients. However, inclusion of the ability to detect and terminate ventricular tachycardias and fibrillation is believed of extreme importance in patients in whom delivery of atrial cardioversion or defibrillation pulses unintentionally in initiates ventricular arrhythmias. Alternatively, the invention may be embodied in a dual chamber pacemaker which does not include a defibrillation or cardioversion pulse generation capability, and employs the invention alone or in conjunction with other pacing level termination therapies as discussed above.

In conjunction with the above specification, we claim:

1. An implantable cardiac pacemaker, comprising:
   means for detection of an atrial tachyarrhythmia.
   means for delivering ventricular pacing pulses at a basic pacing rate in the absence of detected atrial tachyarrhythmia; and
   means responsive to detection of atrial tachyarrhythmia for temporarily delivering ventricular pacing pulses at a rate lower than the basic pacing rate.

2. A pacemaker according to claim 1 further comprising means responsive to detection of atrial tachyarrhythmia for temporarily delivering pacing pulses at a higher rate above the basic pacing rate, prior to delivery of pacing pulses at a rate below the basic pacing rate.

3. A pacemaker according to claim 1 or claim 2 above further comprising means for determining whether delivery of ventricular pacing pulses below the basic pacing rate was successful in terminating the detected atrial tachyarrhythmia.

4. An apparatus according to claim 3 further comprising therapy means for delivering an additional atrial anti-tachyarrhythmia therapy in response to a determination that ventricular pacing below the basic pacing rate was ineffective to terminate the detected atrial tachyarrhythmia.

5. An apparatus according to claim 3 further comprising an inter-therapy timer means for defining an inter-therapy interval following delivery of ventricular pacing pulses at the lower rate and wherein the means for delivering ventricular pacing pulses at the lower rate comprises means for preventing delivery of ventricular pacing pulses at the lower rate during the inter-therapy interval.

6. A pacemaker according to claim 1 or claim 2 above wherein the lower rate is less than one half of the basic rate.

7. A pacemaker according to claim 1 or claim 2 above wherein the lower rate is 0.3 to 0.5 of the basic rate.

8. A pacemaker according to claim 2 above wherein the higher rate is greater than one and one half times the basic rate.

9. A pacemaker according to claim 8 above wherein the higher rate is 1.5–2.5 times the basic rate.

10. A method of cardiac pacing, comprising:

delivering ventricular pacing pulses at a basic pacing rate in an absence of atrial tachyarrhythmia;

detecting an atrial tachyarrhythmia.; and responsive to detection of atrial tachyarrhythmia, temporarily delivering ventricular pacing pulses at a rate lower than the basic pacing rate.

11. A method according to claim 10 further comprising the step of responsive to detection of atrial tachyarrhythmia, temporarily delivering pacing pulses at a higher rate above the basic pacing rate, prior to delivery of pacing pulses at a rate below the basic pacing rate.

12. A method according to claim 10 or claim 11 above further comprising the step of determining whether delivery of ventricular pacing pulses below the basic pacing rate was successful in terminating the detected atrial tachyarrhythmia.

13. A method according to claim 12 further comprising the step of delivering an additional atrial anti-arrhythmia therapy in response to a determination that ventricular pacing below the basic pacing rate was ineffective to terminate the detected atrial tachyarrhythmia.

14. A method according to claim 12 further comprising the steps of defining an inter-therapy interval following delivery of ventricular pacing pulses at the lower rate and preventing delivery of ventricular pacing pulses at the lower rate during the inter-therapy interval.

15. A method according to claim 10 or claim 11 above wherein the step of delivering ventricular pacing pulses at a rate lower than the basic pacing rate comprises delivering ventricular pacing pulses at less than one half of the basic rate.

16. A method according to claim 15 above wherein the step of delivering ventricular pacing pulses at a rate lower than the basic pacing rate comprises delivering ventricular pacing pulses at 0.3 to 0.5 of the basic rate.

17. A method according to claim 11 above wherein the step of delivering ventricular pacing pulses at a rate higher than the basic pacing rate comprises delivering ventricular pacing pulses at greater than one and one half times the basic rate.

18. A method according to claim 17 above wherein the step of delivering ventricular pacing pulses at a rate higher than the basic pacing rate comprises delivering ventricular pacing pulses at 1.5–2.5 times the basic rate.

* * * * *